US00PP29823P3

(12) United States Plant Patent
Byrne et al.

(10) Patent No.: US PP29,823 P3
(45) Date of Patent: Nov. 13, 2018

(54) PEACH TREE NAMED 'FIRE ZEST ONE'

(50) Latin Name: *Prunus persica*
Varietal Denomination: Fire Zest One

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 15/330,678

(22) Filed: Oct. 26, 2016

(65) Prior Publication Data

US 2018/0116083 P1 Apr. 26, 2018

(51) Int. Cl.
*A01H 5/08* (2018.01)
*A01H 6/74* (2018.01)

(52) U.S. Cl.
USPC ..... Plt./197
CPC ..... *A01H 6/7463* (2018.05); *A01H 5/08* (2013.01)

(58) Field of Classification Search
USPC ..... Plt./180, 194, 197
See application file for complete search history.

(56) References Cited

U.S. PATENT DOCUMENTS

| | | | |
|---|---|---|---|
| PP1,884 | P | 11/1958 | Swim |
| PP14,627 | P3 | 3/2004 | Byrne et al. |
| PP14,629 | P3 | 3/2004 | Byrne et al. |
| 2016/0205843 | P1 | 7/2016 | Bryne et al. |

OTHER PUBLICATIONS

UPOV-PLUTO: Plant Variety Database, Nov. 9, 2017, citation for 'Fire Zest One'. 1 page.*
Okie et al. 1985. Peach, Nectarine, and Other Stone Fruit Breeding by the USDA in the Last Two Decades. HortScience 20(4): 633-641.*
Brooks, R.M., Double Delight, Earligoid, and June Gold peaches, 1969, Fruit Varieties J., 13:22.
Brooks et al., Register of New Fruit and Nut Varieties, 1997. 3rd Edition, American Society of Horticultural Science Press, Alexandria, VA.
Byrne et al., Zest peach series: Five medium chill yellow-fleshed cultivars, 2014, HortScience, 49(4):506-508.
Byrne et al., "TexRoyal" a medium chilling peach, 1991, HortScience, 26(10):1338-1340.
Byrne et al., "TexKing" an early ripening medium chill peach, 2004, HortScience, 39(2): 442-443.
Byrne et al., "TexPrince" a mid-season medium chill peach, 2004, HortScience, 39(3):631-632.
Okie, W. R., Handbook of peach and nectarine varieties, 1998, USDA, ARS, Agric, Handbook No. 714.
Rouse et al., "TropicBeauty": a low-chilling peach for subtropical climates, 1989, HortScience, 24:165-166.
Savage et al., Performance of Peach Cultivars in Georgia., 1972, U.S. Department of Agriculture, Research Bulletin 114.
Byrne et al., "TexFirst", An early ripening low chill peach for the subtropics, 2012, HortScience, 47:1803-1804.

* cited by examiner

*Primary Examiner* — Susan McCormick Ewoldt
*Assistant Examiner* — Karen M Redden
(74) *Attorney, Agent, or Firm* — Ramey & Schwaller, LLP

(57) ABSTRACT

Disclosed is a new variety of *Prunus persica* named 'Fire Zest One'. This new fresh market variety, which requires approximately 500-550 chilling units of dormancy, is considered to be a peach tree of early season maturity, which ripens in early May in the medium chill zone of Texas and produces non-melting, yellow fleshed fruit that are very firm, attractively colored, and suitable for both local and long-distance shipping.

6 Drawing Sheets

Latin name: *Prunus persica.*
Variety: Fire Zest One.

BACKGROUND OF THE INVENTION

Field of the Invention

This invention relates to peach trees referred to as a variety of *Prunus persica* named 'Fire Zest One'. 'Fire Zest One', which requires approximately 500-550 chilling units of dormancy, produces very firm, well sized, early ripening and very attractive yellow-fleshed, non-melting peach that matures early in the season. This peach is suitable for fresh market use for consumption.

SUMMARY OF THE INVENTION

The 'Fire Zest One' peach provides a very firm, well sized, early ripening, and very attractive yellow-fleshed peach for the fresh market. The new non-melting flesh peach ripens 65-70 days after full bloom in early May in the medium chill zone of Texas and similar regions.

ORIGIN OF THE VARIETY

The 'Fire Zest One' (TX3A296) peach [*Prunus persica* (Batsch) L.] was selected from a population of seedlings from a cross between the female parent, TX2B1 (not released or patented), an early ripening high color selection and the early ripening, non-melting yellow flesh peach 'Spring Baby' (not patented, Okie, 1998) as the male parent. The cross was made in 2002, planted in 2004 and TX3A296 was selected in 2005 from the high density seedling selection block in College Station, Tex. TX2B1 is a selection from a population of seedlings created by crossing the female parent 'TropicBeauty' (not patented, Rouse and Sherman, 1989), a low chill, yellow-fleshed peach with the male parent 'Springold' (not patented, Savage and Prince, 1972), an early ripening peach used in the southeastern USA. 'Spring Baby', a release from the USDA Stone Fruit Breeding Program in Parlier, Calif., was developed by crossing two unreleased selections (P51-2 and P51-103, not patented) which were both selected from an open pollinated population from the female parent 'Springcrest' (not patented, Savage and Prince, 1972).

'Fire Zest One' differs from its male parent 'Spring Baby' as it blooms 7-10 days earlier and ripens with it in the medium chill zone of Texas. As compared to its female parent, TX2B1, it blooms 10-14 days after and ripens about 5 days before it in the medium chill zone of Texas. As compared to 'Spring Baby', 'Fire Zest One' generally is more attractive with more blush and a rounder shape.

Two-year and older trees of the variety were subsequently evaluated during the 2007 through 2013 fruit growing seasons in California (Clovis) and during the 2009 through 2015 fruit growing seasons in Texas (College Station and Fairfield).

ASEXUAL REPRODUCTION OF THE VARIETY

'Fire Zest One' was bud grafted onto virus-free Nemaguard (not patented, Brooks and Olmo, 1997) peach rootstock in June 2005 at the nursery site in Oakdale, Calif. The variety was subsequently planted at the experimental orchard in the central portion of the San Joaquin Valley, near Fowler, Fresno County, Calif. and in two sites in Texas (College Station and Fairfield). Fruit from the resulting propagation has been evaluated during the period from 2009 to 2013 fruit seasons. This evaluation clearly demonstrated that the re-propagated trees were true to the characteristics of the original seedling in all observable aspects.

BRIEF DESCRIPTION OF THE DRAWINGS

This new variety of peach tree is illustrated by the accompanying photographic drawings and depicts the plant by the best possible color representation using color photography, wherein.

BOTANICAL DESCRIPTION OF THE VARIETY

Figure 1:
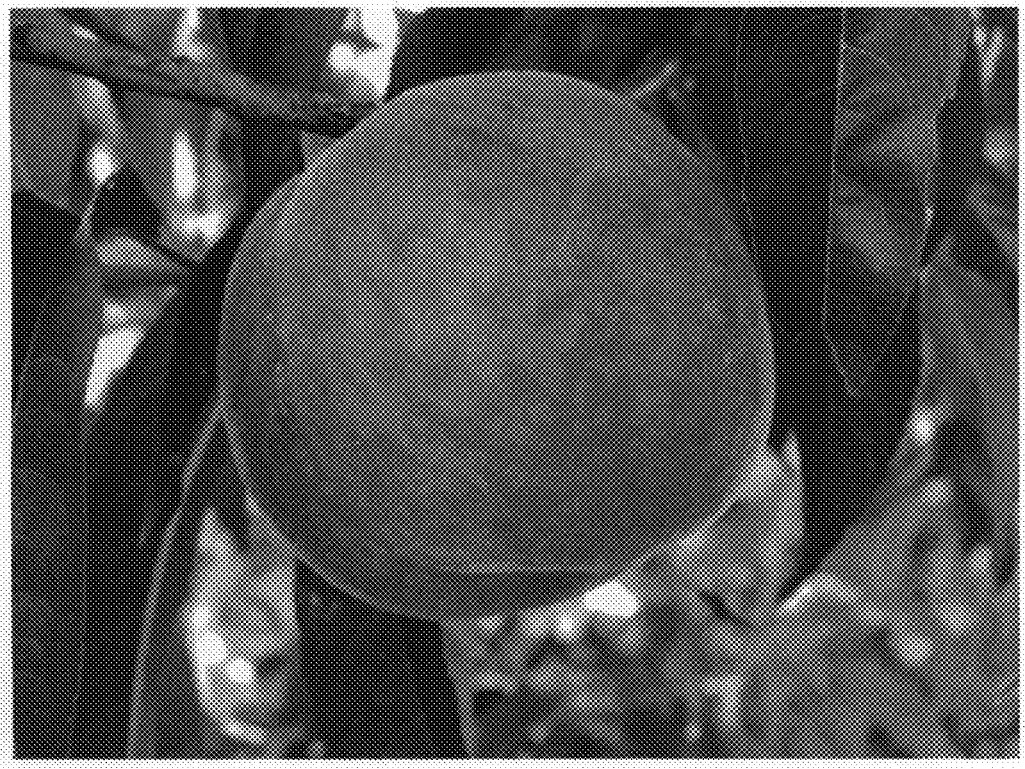
FIG. 1. 'Fire Zest One' fruit on a five-year old tree in the research plots in Clovis, Calif. showing the high external coloration and the round symmetrical shape of the fruit.
Figure 2:
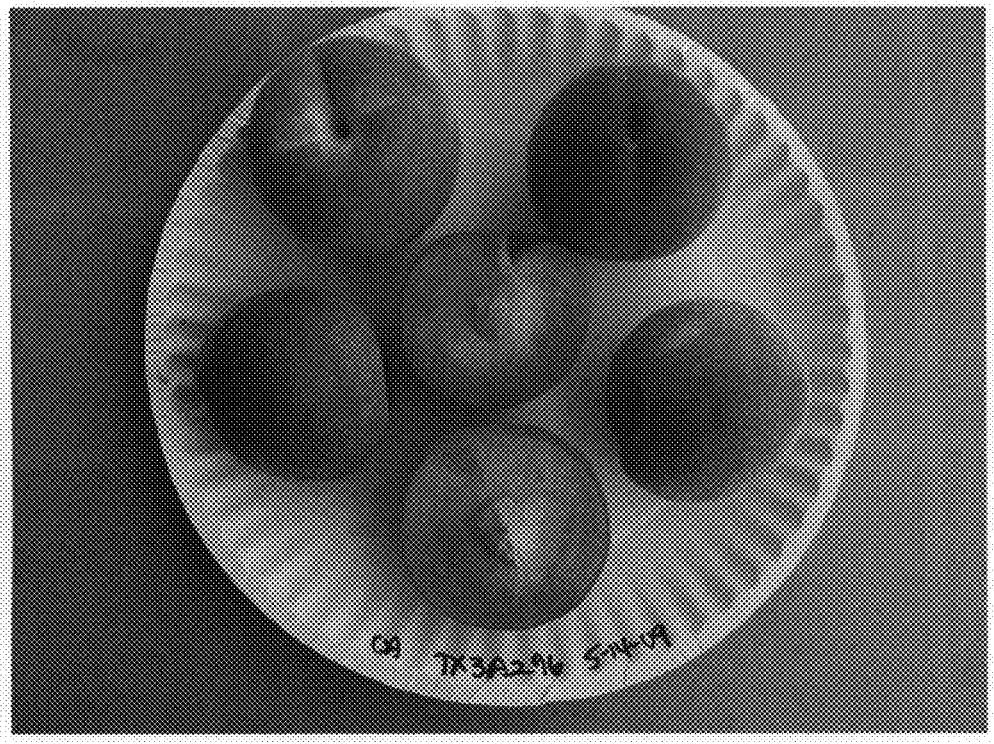
FIG. 2. Sample of 'Fire Zest One' showing the round symmetrical shape and the internal and external coloration of the fruit.
Figure 3:
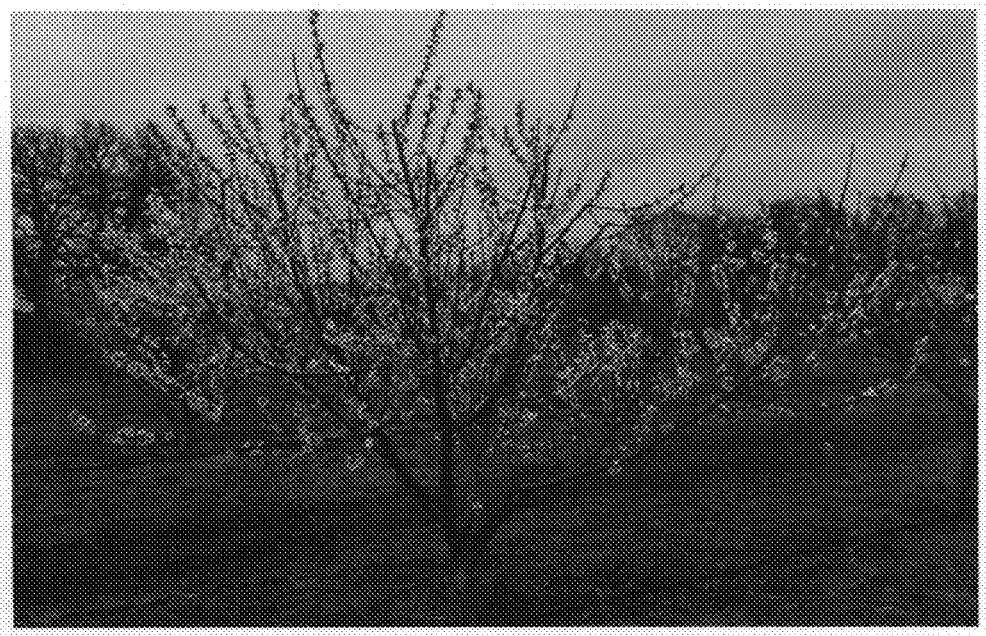
FIG. 3. 'Fire Zest One' tree (three-year old) in full bloom in Fairfield, Tex.
Figure 4:
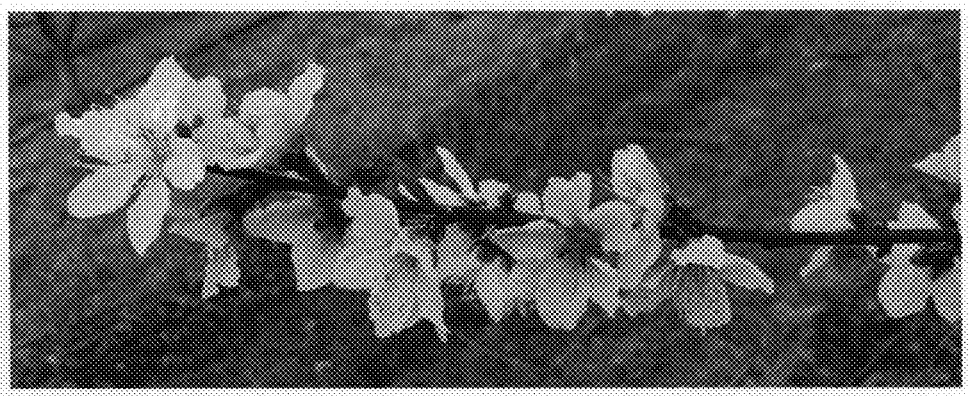
FIG. 4. 'Fire Zest One' branch with flowers showing the large showy light pink flowers on a three-year old tree.
Figure 5:
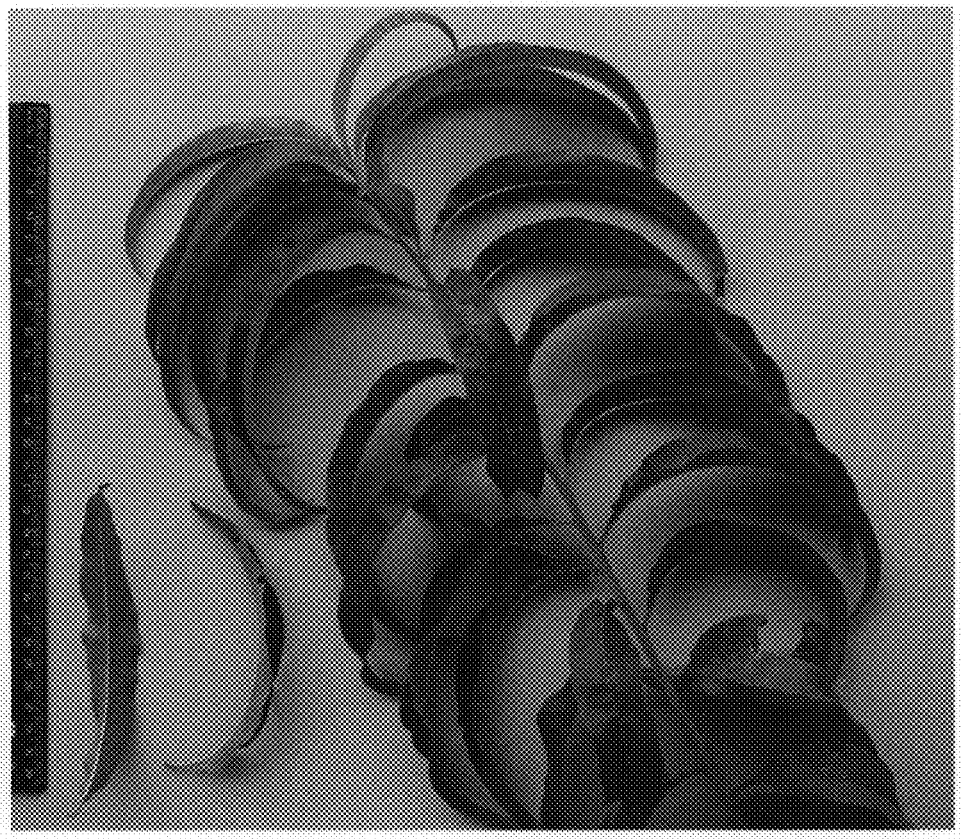
FIG. 5. Color photograph of a one-year old shoot and leaves showing both adaxial and abaxial surfaces from a three-year-old tree of 'Fire Zest One' grown in College Station, Tex. The ruler is demarcated in millimeters.
Figure 6:
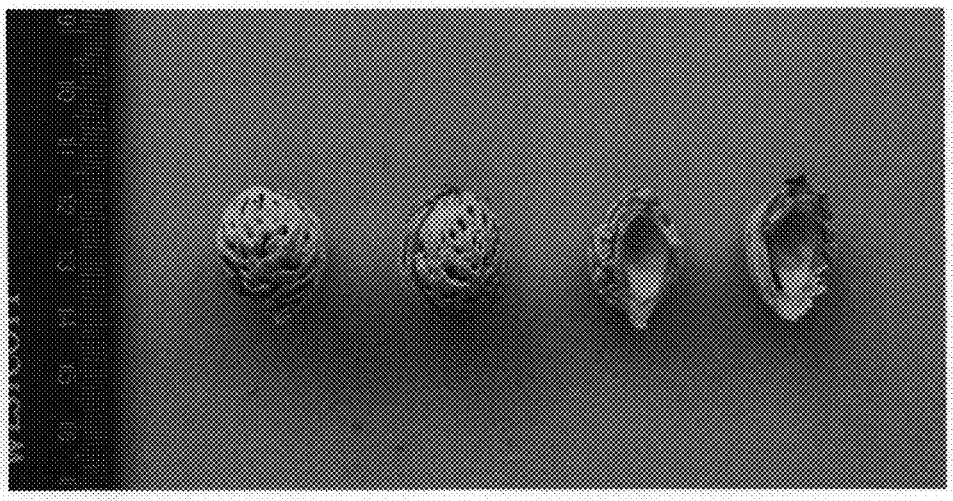
FIG. 6. Color photograph showing the pits (endocarp) of 'Fire Zest One'. The ruler is demarcated in millimeters.

Referring more specifically to the pomological details of this new and distinct variety of peach tree, the following has been observed under the ecological conditions prevailing at the experimental orchards in medium chill zone of Texas in College Station and Fairfield. All major color code designations are by reference to The R.H.S. Colour Chart (2001) provided by The Royal Horticultural Society of Great Britain. Colors are approximate as color depends on horticultural practices such as light level and fertilization rate, among others.

Tree:

*Size*.—Generally average to above average as compared to other common peach cultivars ripening in the early season of maturity.

*Height*.—8-10 feet (2.4-3 m) at the end of the 2016 growing season on a three-year old tree.

*Width*.—5-6 feet width (1.5-1.8 m) at the end of the 2016 growing season on a three-year old tree.

*Vigor*.—High.

*Density*.—Medium to high.

*Productivity*.—Productive.

*Shape*.—The trees are vigorous with the typical semi-spreading growth habit similar to 'TexKing' (U.S. Plant Pat. No. 14,627), 'TexPrince' (U.S. Plant Pat. No. 14,629), and 'TexRoyal' (not patented, Byrne and Bacon, 1991).

*Current season growth*.—The current season growth for the new variety was approximately 3.5 to 5 feet (1.1-1.5 m) on a three-year old tree.

*Regularity of bearing*.—Regular, and considered hardy under typical environmental conditions in the medium chill zone of Texas and the central San Joaquin Valley, Calif. conditions.

Trunk:

*Size*.—Approximately 2.75 inches (7 cm) in diameter when measured at a distance of approximately 12 inches (30.5 cm) above the soil level, at the end of the 2016 growing season on a three-year old tree.

*Bark texture*.—Considered moderately rough with numerous folds of papery scarf-like skin being present.

*Bark coloration*.—Medium brown with grey. Colors present are N155A of the White Group and 165A, 166A-B, 175A-D and 176A of the Greyed-Orange Group.

Branches:

*Size*.—Considered medium for the variety.

*Thickness*.—Average (about 3.2 to 4.5 cm in diameter as measured 10 cm from the trunk on a three-year old tree) as compared to other varieties.

*Length*.—The length of the branches is limited by pruning to a 3 to 5 foot (~0.9-1.5 m) length depending on the position in the tree.

*Surface texture*.—Average and appearing furrowed on wood that is several years old.

*Lenticels*.—Numerous flat, oval lenticels present. The lenticels range in size from approximately 2 to 6 mm in width and were approximately 1 to 1.5 mm in height.

*Current season shoots*.—Surface texture — Substantially glabrous.

*Internode length*.—Approximately 1.5 to 2.5 cm as measured in the middle of a current season stem.

*Color of mature branches*.—The predominant colors are medium brown, 165A of the Greyed-Orange Group, N199C-D of the Grey-Brown Group and 200D of the Brown Group.

*Current season shoots*.—Color — Light brown (164A, 165B-C and 166C-D of the Greyed-Orange Group). The color of new shoot tips is considered medium green (144B-C of the Yellow-Green Group) with some reddish-brown coloration appearing on exposed surface of the shoots (173A of the Greyed-Orange Group and 178B-C and 179A of the Greyed-Red Group).

*Type of bearing shoot*.—Long shoots only.

*Spur length*.—Not applicable.

Leaves:

*Size*.—Considered medium for the species. Leaf measurements have been taken from vigorous upright current season growth approximately at mid-shoot on three-year old trees.

*Leaf length*.—Approximately 165 to 175 mm.

*Leaf width*.—Approximately 29 to 32 mm.

*Leaf thickness*.—Less than 1 mm.

*Leaf form*.—Lanceolate.

*Leaf tip form*.—Acuminate.

*Leaf upper surface color*.—Green, varying among 137C of the Green Group and 146A-B of the Yellow-Green Group.

*Leaf lower surface color*.—Green, varying among 146C-D of the Yellow-Green Group.

*Leaf mid-vein color*.—Light yellow green, varying among 145C and 154D of the Yellow-Green Group.

*Leaf margins*.—

*Form*.—Considered crenate.

*Uniformity*.—Considered generally uniform.

*Leaf petioles*.—

*Size*.—Considered short to medium.

*Length*.—Approximately 8 to 9 mm.

*Thickness*.—Approximately 1 to 1.5 mm.

*Color*.—Pale green, varying among 145C and 154D of the Yellow-Green Group.

*Leaf glands*.—

*Size*.—Less than 1 mm in height and width.

*Number*.—Generally 1 to 2 per leaf.

*Type*.—Globose.

*Color*.—Light green, varying among 145C and 154D of the Yellow-Green Group with dark brown N199B-C of the Grey-Brown Group and 200D of the Brown Group.

*Leaf stipules*.—

*Size*.—Medium to large for the species.

*Length*.—Approximately 14 to 16 mm.

*Width*.—Less than 1 mm.

*Form*.—Lanceolate.

*Color*.—Light green, N144A-C of the Yellow-Green Group developing a reddish brown color upon advancing maturity 178B of the Greyed-Red Group and 185A of the Greyed-Purple Group. The stipules are considered to be early deciduous.

*Ratio of wood (leaf) buds to flowering buds*.—1 to 2 flower buds per vegetative bud.

Flowers:

*Floral buds*.—

*General*.—The floral buds are considered to be medium to medium large in size, conic in form, and slightly appressed relative to the bearing shoot.

*Color*.—The bud scales are brown, (approximately 187A-B of the Greyed-Purple Group and 200A-C and N200A of the Brown Group). The buds are considered hardy under the typical climatic conditions found in the medium chill zone of Texas and the central San Joaquin Valley, Calif.

*Length*.—Approximately 5 mm on flower buds in late summer on current season wood.

*Width*.—Approximately 2 mm on flower buds in late summer on current season wood.

*Blooming type*.—Considered early in relation to other peach cultivars commonly growing in the medium chill zone of Texas and the central San Joaquin Valley. Date of full bloom was between February 18th and February 27th during the period between 2009 and 2015. In the medium chill sites (College Station and Fairfield, Tex.), this peach bloomed about 5 days after the medium chill peach 'TexKing' (U.S. Plant Pat. No. 14,627, Byrne and Bacon, 2004), with the peach 'Royal Zest Two' (U.S. Plant Pat. No. 28,172, Byrne and Anderson, 2014) and 8-14 days before 'June Gold' (U.S. Plant Pat. No. 1,884; Brooks, 1958). It is estimated that the chilling requirement is between 500-550 CU.

*Flower fertility*.—Self-fertile.

*Flower type*.—Showy.

*Flower size*.—Flower diameter at full bloom is approximately 32 to 44 mm.

*Bloom quantity*.—Considered abundant.

*Flower bud frequency*.—Normally 1 to 2 per node.

*Petal size*.—

*General*.—Considered medium large for the species.

*Width*.—Approximately 12 to 14 mm.

*Length*.—Approximately 20 to 22 mm.

*Petal form*.—Broadly ovate.

*Petal count*.—Nearly always 5.

*Petal color*.—Light pink when young (Red-Purple Group 69B-C; Purple Group 75D), becoming slightly darker near the petal claw.

*Petal claw*.—

*Form*.—The claw is considered truncate in shape and has a medium size when compared to other varieties.

*Length*.—Approximately 1 to 1.5 mm.

*Width*.—Approximately 1 mm.

*Petal margins*.—Generally considered variable, from nearly smooth to slightly undulate.

*Petal apex*.—Generally — The petal apices appear slightly domed.

*Flower pedicel*.—

*Length*.—Considered medium to short, and having an average length of approximately 2 to 4 mm.

*Thickness*.—Considered average, approximately 1 mm.

*Color*.—A light green (Yellow-Green Group 144D and N144B-D).

*Floral nectaries*.—

*Color*.—Variable, from white to light yellow (Yellow Group 2D, 3D, 4C-D and 5D; White Group 155A-D).

*Hypanthium*.—

*Surface texture*.—Generally glabrous.

*Color.*—A brownish red to maroon with green (Red Group 46A and 53A; Yellow-Green Group 144A-B and 145A; Greyed-Orange Group 176A; Greyed-Red Group 178A-B; Greyed-Red Group 181A; Greyed-Purple Group 183A-C, 185A and 187C).

*Sepals.*—

*Surface texture.*—The surface has a short, fine, wooly texture.

*Size.*—Slightly smaller than average, and ovate in form.

*Length.*—4.8 to 5.7 mm on recently opened flowers.

*Width.*—3.9 to 5.2 mm on recently opened flowers.

*Color.*—A brownish red to maroon with green and grey (Red Group 46A and 53A; Yellow-Green Group 144A-B and 145A; Greyed-White Group 156A-D; Greyed-Orange Group 176A; Greyed-Red Group 178A-B; Greyed-Red Group 181A; Greyed-Purple Group 183A-C, 185A and 187C).

*Anthers.*—

*General.*—Average in size for the species. The anthers are about 1 mm in length and 0.5 mm in width.

*Color.*—Young anthers are reddish-orange with white and yellow (White Group 155A-D; Yellow-White Group 158A-D; Greyed-Orange Group N163A, 168A, 169A-B, 170A, 171B and N172A-B).

*Pollen production.*—Pollen is abundant, and is a yellow color (approximately Yellow Groups 5A-B and 12A-13B).

*Filaments.*—

*Size.*—Variable in length, approximately 13 to 15 mm, with the filaments equal to or slightly longer than the pistil.

*Color.*—White when young (approximately White Group 155A-D and N155C-D) and darkening to medium pink (Red-Purple Group 63B-C and 64D) with advanced maturity.

*Pistil.*—

*General.*—Average in size, but equal to or slightly shorter to the general anther height, overall.

*Length.*—Approximately 15 to 16 mm, including the ovary.

*Color.*—Considered a very light yellow-green when young (Yellow Group 1C-D and Yellow-Green Group 151A), and developing a medium-dark pink coloration (Red-Purple Group N57D, 62B-C and 63C) with advancing senescence.

*Surface texture.*—None present.

Fruit:

*Maturity when described.*—The present variety of fruit is described as it would be found in its firm ripe condition at full commercial maturity under the ecological conditions prevailing in the medium chill zone of Texas. This early ripening, clingstone, non-melting flesh peach cultivar ripens 65-70 days after full bloom which generally is in the first week of May in the medium chill zone of Texas. It ripens with 'Victor' (UPOV PBR PRUNU_PER grant #25391), 7-12 days before 'TexKing' (U.S. Plant Pat. No. 14,627), and about 19 days before 'Royal Zest Two' (U.S. Plant Pat. No. 28,172).

*Fruit quality.*—This cultivar has very good size, good to excellent quality and excellent attractiveness for an early ripening peach when properly managed and thinned. TX3A296 has medium acidity, very good storage characteristics and its mean soluble solids is similar to other commercial cultivars such as 'Tex-First' (U.S. Plant Pat. No. 26,119; Byrne and Anderson, 2012), 'Texking', and 'Royal Zest Two' when picked mature.

*Size.*—General — Medium-large to large for the season and considered uniform.

*Average cheek diameter.*—Approximately 53 to 56 mm.

*Average suture diameter.*—Approximately 52 to 54 mm.

*Average axial diameter.*—Approximately 52 to 54 mm.

*Average fruit weight.*—125 grams.

*Fruit form.*—Generally considered truncate with unequal halves. Occasionally the fruit exhibits less symmetry when comparing the suture height with the line opposite the suture. The fruit is generally uniform in symmetry when viewed from the apical aspect.

*Fruit suture.*—Generally, the suture appears as a thin line that extends from the base to the apex, and appears deeper at the apex, forming a shallow basin at the apical point. No apparent callusing or stitching exists along the suture line.

*Color.*—Deep red, 53A of the Red Group, 59A-B of the Red-Purple Group and 183A-B, 185A and 187A-B of the Greyed-Purple Group.

*Ventral surface.*—Form — Considered uniform.

*Stem cavity.*—

*Size.*—Considered moderately shallow for the species.

*Width.*—Approximately 13 to 17 mm.

*Length.*—Approximately 17 to 20 mm.

*Depth.*—Approximately 8 mm.

*Form.*—Considered variable but generally round.

*Fruit base.*—Flat.

*Fruit apex.*—Round.

*Fruit stem.*—

*Length.*—Approximately 9 mm.

*Thickness.*—Approximately 3 mm.

*Color.*—Medium green, from 143C of the Green Group to 144A-B, N144C and 146C of the Yellow-Green Group.

*Fruit skin.*—Generally considered medium or average in thickness.

*Surface texture.*—Light, short pubescence.

*Skin acidity.*—Considered neutral.

*Tenacious to flesh.*—Yes at commercial maturity.

*Tendency to crack.*—No cracking observed.

*Skin color.*—Generally — Variable, with a high (~70-90%) percentage of the fruit surface covered with a blush as described below under Blush Color.

*Pubescence.*—Light and short.

*Blush color.*—Deep red, 53A of the Red Group; 178A-B and 180A-B of the Greyed-Red Group; 183A-C, 187A-C and 185A of the Greyed-Purple Group.

*Skin ground color.*—Medium orange, 19A, 20A and 22A-B of the Yellow-Orange Group.

*Flesh color.*—Medium to light yellow, 11C-D, 12D and 13D of the Yellow Group and 14D, 16D, 18B-C and 19C-D of the Yellow-Orange Group.

*Flesh fibers.*—Present, numerous, and lightly colored. These fibers are present throughout the flesh.

*Stone cavity color.*—12D of the Yellow Group and 14D and 18A-B of the Yellow-Orange Group.

*Flesh texture*.—Generally, the flesh is considered firm and fine at commercial maturity.

*Ripening*.—Generally the fruit of the present variety ripens evenly.

*Flavor*.—Considered sweet with slightly acidic flavor.

*Soluble solids*.—Varies from 9 to 14 Brix depending on the site, weather, and cultural care.

*Acidity*.—Generally varies between 5.7 to 8.0 meq/mL.

*Aroma*.—Pleasant and reasonably abundant.

*Eating*.—Generally considered very good to excellent, particularly for an early ripening variety.

Stone:

*Attachment*.—Clingstone (strongly adherent) at commercial maturity.

*Stone size*.—Generally considered small to medium relative to the ratio of stone to fruit size.

*Length*.—Approximately 26 to 31 mm.

*Width*.—Approximately 19 to 26 mm.

*Thickness*.—Approximately 15 to 19 mm.

*Stone form*.—Round to elliptical.

*Stone base*.—The stone is narrow to medium.

*Base angle*.—The base angle of the stone is variable, but most frequently is considered slightly oblique to the stone axis.

*Hilium*.—Generally considered medium in size, and rather poorly defined as is common in very early ripening varieties. The hilum is approximately 4 to 6 mm long and 1 to mm or less wide.

*Form*.—Considered oval.

*Apex shape*.—Narrow to medium.

*Stone shape*.—Considered variable. The stone is normally ovoid to elongated.

*Stone surface*.—

*Surface texture*.—Single pits and rosettes of pits.

*Ridges*.—Numerous fine ridges are present basally, and converge towards the base of the stone.

*Ventral edge*.—Small to medium.

*Dorsal edge*.—Shape — Grooved and having moderately rough edges.

*Stone color*.—The color of the dry stone is light brown, 164D and 165C-D of the Greyed-Orange Group. The color of the inside surface of the endocarp is primarily 164D and 165D of the Greyed-Orange Group.

*Tendency to split*.—Splitting has not been observed.

*Kernel*.—The kernel fills the endocarp at harvest and measures approximately 4 to 5 mm in thickness, 9 mm in width, and 14 to 15 mm in length. When dried the kernels measure approximately 1 to 1.5 mm in thickness, 7 mm in width, and 12 mm in length. The colors of the dried kernels are primarily 164A, 165B-C, 166D and N167A-D of the Greyed-orange Group. The seed is not viable.

*Use*.—The subject variety, 'Fire Zest One', is considered to be a peach tree of early-season maturity, which produces fruit which are very firm, attractively colored, and which are useful for both local and long distance shipping.

*Keeping quality*.—Very good.

*Resistance to insects and disease*.—No particular susceptibilities were noted or claimed. No observations have been made on resistance for either peach rust (*Tranzschelia discolor*) or bacterial leaf spot [*Xanthomonas campestris* pv. *pruni* (E. F. Smith) Dye].

*Shipping quality*.—Very good.

Although the new variety of peach tree possesses the described characteristics when grown under the ecological conditions prevailing near College Station and Fairfield, Tex., it will be understood that variations of the usual magnitude and characteristics incident to the changes in growing conditions, fertilization, pruning, and pest control are to be expected.

REFERENCES

Anon. 2001. R.H.S. Colour Chart. The Royal Hort. Soc., London.

Brooks, R. M. 1958. Double Delight, Earligold, and June Gold peaches. Fruit Var. J. 3:22. U.S. Plant Pat. No. 1,884.

Brooks, R. M. and H. P. Olmo. 1997. Register of New Fruit and Nut Varieties. 3rd Edition. American Society of Horticultural Science Press, Alexandria, Va.

Byrne, D. H. and N. Anderson. 2014. Zest peach series: Five medium chill yellow-fleshed cultivars. HortScience 49(4):506-508.

Byrne, D. H and N. Anderson. Peach tree, Royal Zest Two. U.S. Plant Pat. No. 28,172, Jul. 11, 2017.

Byrne, D. H. and T. A. Bacon. 1991. 'TexRoyal', a medium chilling peach. HortScience 26(10):1338-1340.

Byrne, D. H. and T. A. Bacon. 2004. 'TexKing', an early ripening medium chill peach. HortScience 39: 442-443. U.S. Plant Pat. No. 14,627. Mar. 23, 2004.

Byrne, D. H. and T. A. Bacon. 2004. 'Texprince', a mid season, medium chill peach. HortScience 39(3):631-632. U.S. Plant Pat. No. 14,629. Mar. 23, 2004.

Okie, W. R. 1998. Handbook of peach and nectarine varieties, USDA, ARS, Agric. Handbook No. 714.

Rouse, R. and W. Sherman. 1989. 'TropicBeauty': a low-chilling peach for subtropical climates. HortScience 24:165-166.

Savage, E. F. And V. E. Prince. 1972. Performance of Peach Cultivars in Georgia. U.S. Department of Agriculture, Research Bulletin 114.

We claim:

1. A new and distinct *Prunus persica* tree, substantially as illustrated and described herein.

* * * * *